US012329904B2

(12) United States Patent
Petit et al.

(10) Patent No.: US 12,329,904 B2
(45) Date of Patent: Jun. 17, 2025

(54) NASAL POWDER DELIVERY DEVICE

(71) Applicant: APTAR FRANCE SAS, Le Neubourg (FR)

(72) Inventors: Ludovic Petit, Vitot (FR); Franck Poullain, La Haye Malherbe (FR)

(73) Assignee: APTAR FRANCE SAS, Le Neubourg (FR)

(*) Notice: Subject to any disclaimer, the term of this patent is extended or adjusted under 35 U.S.C. 154(b) by 834 days.

(21) Appl. No.: 17/625,439

(22) PCT Filed: Jul. 9, 2020

(86) PCT No.: PCT/FR2020/051225
§ 371 (c)(1),
(2) Date: Jan. 7, 2022

(87) PCT Pub. No.: WO2021/005308
PCT Pub. Date: Jan. 14, 2021

(65) Prior Publication Data
US 2022/0362491 A1 Nov. 17, 2022

(30) Foreign Application Priority Data
Oct. 7, 2019 (FR) ..................................... 1907764

(51) Int. Cl.
A61M 15/08 (2006.01)
A61M 11/00 (2006.01)
(Continued)

(52) U.S. Cl.
CPC .......... A61M 15/08 (2013.01); A61M 11/007 (2014.02); A61M 11/02 (2013.01);
(Continued)

(58) Field of Classification Search
CPC .............. A61M 15/00; A61M 15/0028; A61M 15/0061; A61M 15/08; A61M 11/00; A61M 11/007; A61M 11/02; B05B 11/02
See application file for complete search history.

(56) References Cited

U.S. PATENT DOCUMENTS 5,284,132 A    2/1994  Geier
10,653,690 B1 * 5/2020  Savmarker ........... A61K 9/1617
(Continued)

FOREIGN PATENT DOCUMENTS

FR      2 684 304 A1   6/1993
WO      91/12895 A1    9/1991
(Continued)

OTHER PUBLICATIONS

International Preliminary Report on Patentability with the translation of Written Opinion dated Jan. 11, 2022 from the International Bureau in International Application No. PCT/FR2020/051225.
(Continued)

Primary Examiner — Joseph D. Boecker
(74) Attorney, Agent, or Firm — Sughrue Mion, PLLC

(57) ABSTRACT

A nasal delivery device for a powder, having a reservoir, a delivery head and an air discharge system generating a flow of compressed air. The air discharge system has an air chamber, formed by a hollow axial cylinder, and a piston that sealingly slides in the air chamber to compress the air. The hollow axial cylinder has a radial shoulder connecting a first cylinder portion and a second cylinder portion. Before actuation, the piston is at the first cylinder portions and, during actuation, the piston sealingly cooperates with the second cylinder portion. The radial shoulder defines a profile that the piston overcomes at start of actuation. The piston has an upper lip and a lower lip, a skirt around the hollow axial cylinder with a lower flange projecting radially inward. The
(Continued)

Figure 1:
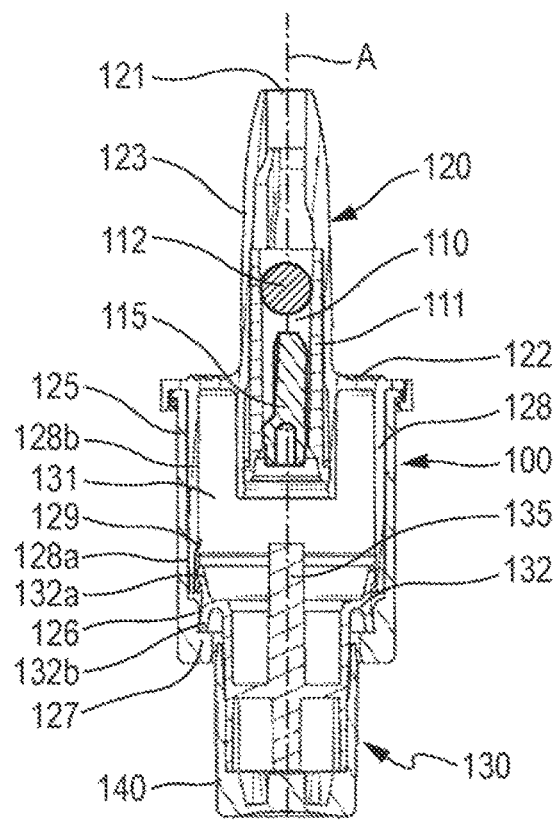

skirt has a profile radially projecting towards the inside, cooperating before actuation with the lower lip of the piston.

5 Claims, 2 Drawing Sheets

(51) Int. Cl.
  *A61M 11/02* (2006.01)
  *A61M 15/00* (2006.01)
  *B05B 11/02* (2023.01)
(52) U.S. Cl.
  CPC ......... *A61M 15/0028* (2013.01); *B05B 11/02* (2013.01); *A61M 15/0061* (2014.02); *A61M 2202/064* (2013.01); *A61M 2205/073* (2013.01); *A61M 2210/0618* (2013.01)

(56) References Cited

U.S. PATENT DOCUMENTS

| 2016/0082455 A1* | 3/2016 | Baillet | ................. B05B 11/062 222/216 |
| 2016/0167071 A1* | 6/2016 | Baillet | ................. B05B 11/06 222/23 |
| 2016/0296957 A1* | 10/2016 | Baillet | ................. B05B 11/0029 |
| 2022/0257884 A1* | 8/2022 | Poullain | ............ A61M 15/0061 |

FOREIGN PATENT DOCUMENTS

| WO | 99/46055 A1 | 9/1999 |
| WO | 02/45866 A1 | 6/2002 |
| WO | 2015/001281 A1 | 1/2015 |
| WO | WO-2017118827 A1 * | 7/2017 | ............ A61M 11/02 |
| WO | 2018/051371 A2 | 3/2018 |

OTHER PUBLICATIONS

International Search Report for PCT/FR2020/051225 dated Jan. 15, 2021.
Written Opinion for PCT/FR2020/051225 dated Jan. 15, 2021.

* cited by examiner

NASAL POWDER DELIVERY DEVICE

CROSS REFERENCE TO RELATED APPLICATIONS

This application is a National Stage of International Application No. PCT/FR2020/051225 filed Jul. 9, 2020, claiming priority based on French Patent Application No. 1907764 filed Jul. 10, 2019.

The present invention relates to a nasal powder delivery device.

Nasal powder delivery devices are well-known. They generally comprise a reservoir containing one or more doses of powder, delivery means, and a nasal delivery head intended to be inserted in a nostril of a user, said nasal delivery head comprising a delivery aperture. The delivery means generally comprise an air discharge system. When the delivery device is actuated, a dose of powder is delivered into a nostril of the user.

A disadvantage with these devices of the prior art relates to the reliability of the device, in particular before and upon actuation. Thus, to maintain the device in the non-actuated state during transport and/or in case of accidental fall, generally breakable bridges are provided between two mobile portions against one another upon actuation. These breakable bridges have several disadvantages: they are difficult to mould, and the breaking force is difficult to control. In addition, due to their static state before breaking, they are likely to be broken in case of the device accidentally falling.

Documents WO9946055, WO0245866, WO2015001281, WO2017118827, WO2018051371, WO9112895, U.S. Pat. No. 5,284,132 and FR2684304 describe the devices of the state of the art.

The present invention aims to provide a nasal powder delivery device which does not reproduce the abovementioned disadvantages.

The present invention also aims to provide a nasal powder delivery device which improves the reliability of the device before and upon actuation.

The present invention also aims to provide a nasal powder delivery device which is simple and inexpensive to manufacture and to assemble.

The present invention also aims for a nasal powder delivery device comprising a reservoir containing at least one dose of powder, a nasal delivery head intended to be inserted in a nostril of a user, said nasal delivery head comprising a delivery aperture, and an air discharge system generating, upon actuation of said nasal powder delivery device, a flow of compressed air to deliver a dose of powder in said nostril through said delivery aperture, said air discharge system comprising an air chamber, formed by a hollow axial cylinder, and a piston which upon actuation of the device, sealingly slides in said air chamber to compress the air contained in said air chamber, said hollow axial cylinder comprising a radial shoulder which connects a first cylinder portion of larger diameter and a second cylinder portion of smaller diameter, said piston being arranged before actuation at said first cylinder portion, and upon actuation, said piston sealingly cooperates with said second cylinder portion, to compress the air contained in said air chamber and thus generate the flow of compressed air, said radial shoulder defining in said hollow axial cylinder, a profile that said piston must overcome at the start of actuation, said piston comprising an upper lip and a lower lip, a skirt being arranged around said hollow axial cylinder, said skirt comprising, in the vicinity of its axially lower edge, a lower flange, which radially projects inwards, said skirt comprising, in the vicinity of said lower flange, at least one profile which radially projects inwards, cooperating before actuation with said lower lip of said piston.

Advantageously, before actuation, said piston can be moved between two non-actuated positions, a lower transport position, in which said lower lip of said piston is abutted against said lower flange of said skirt, and an upper transport position, in which said upper lip of said piston is abutted against said radial shoulder of said hollow cylinder.

Advantageously, said profiles are formed by one or more axial ridges distributed over the periphery of said skirt.

Advantageously, said air chamber is opened to the atmosphere before actuation.

Advantageously, said reservoir contains one single dose of powder, delivered upon one single actuation of said nasal powder delivery device.

Figure 2:
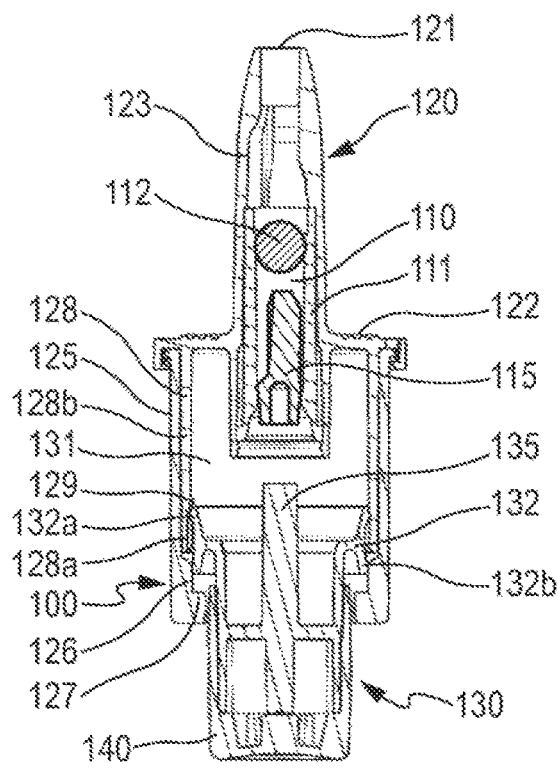
Figure 3:
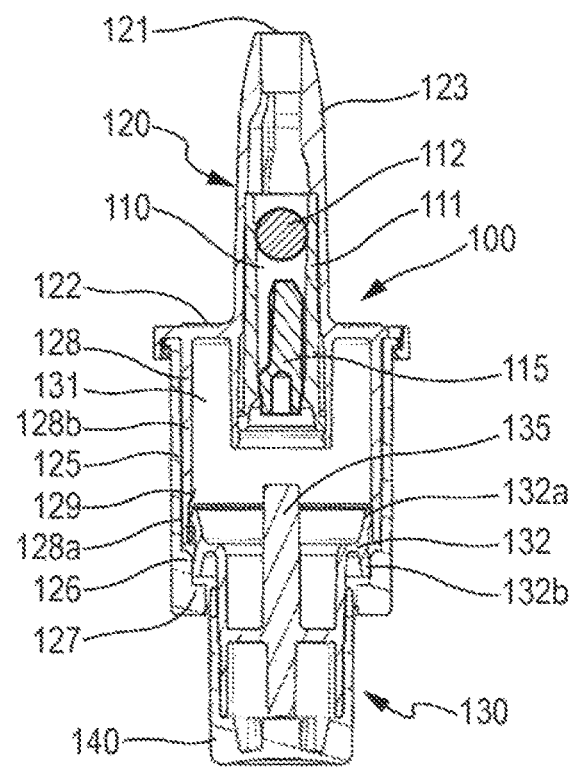
Figure 4:
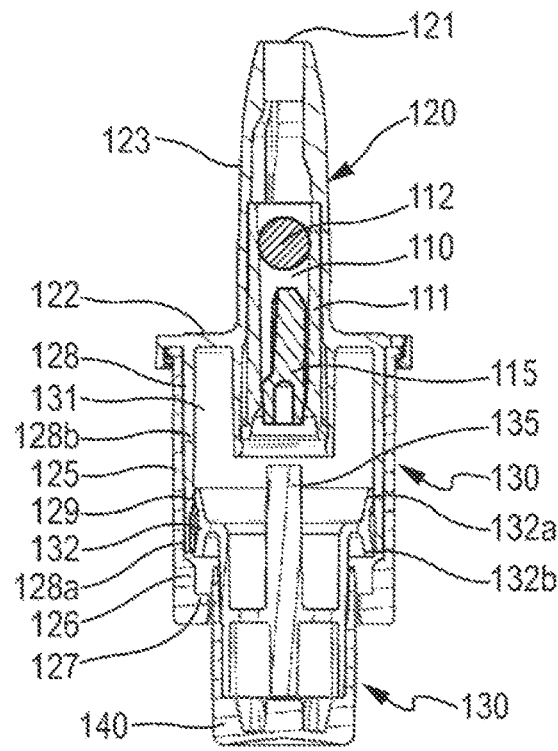
Figure 5:
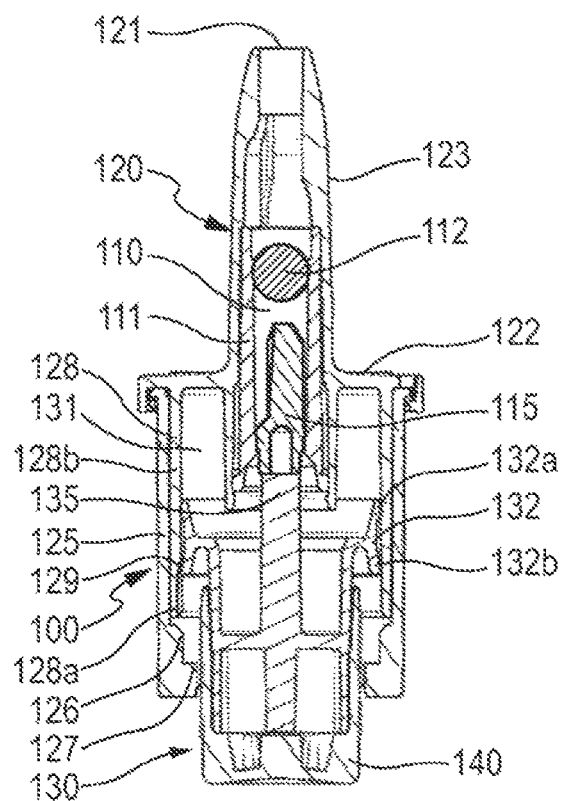
Figure 6:
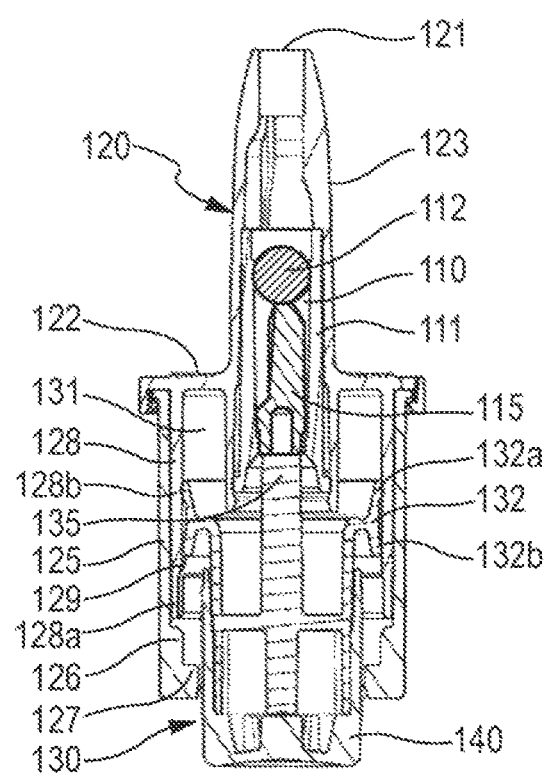
Figure 7:
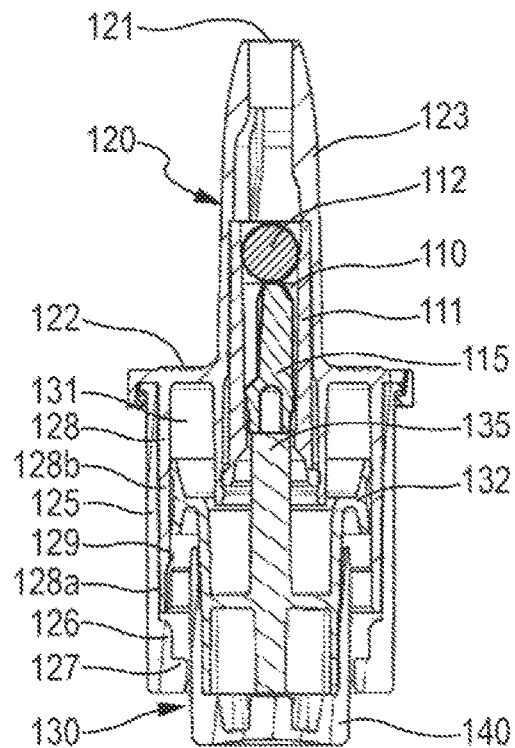
Figure 8:
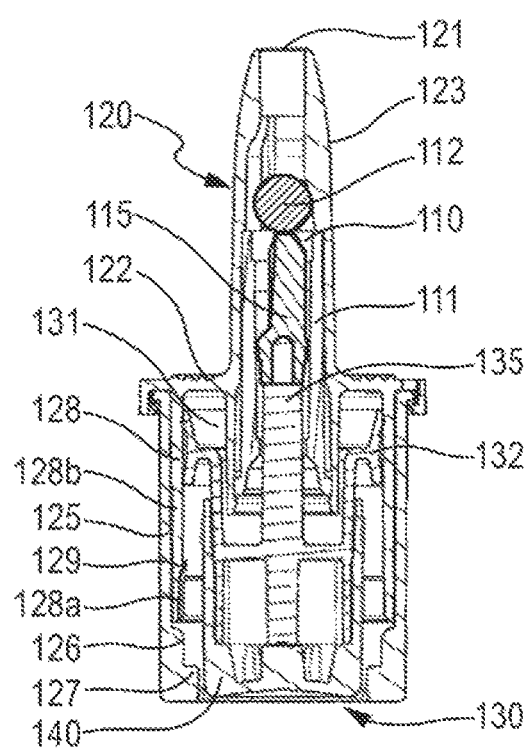

These characteristics and advantages and others will appear more clearly in the following detailed description, made in reference to the appended drawings, given as non-limiting examples, and in which:

FIGS. 1 and 2 are schematic cross-sectional views of a nasal powder delivery device according to one advantageous embodiment, respectively in lower and upper transport position, FIG. 3 is a view similar to those in FIGS. 1 and 2, in rest position, before actuation, FIG. 4 is a view similar to that of FIG. 3, at the start of actuation, FIGS. 5 to 7 are views similar to that of FIG. 3, showing different positions upon actuation, and FIG. 8 is a view similar to that of FIG. 3, at the end of actuation.

In the description, the terms "axial" and "radial" refer to the longitudinal axis A of the device represented in FIG. 1. The terms "proximal" and "distal" refer to the delivery aperture of said device. The terms "top", "bottom", "upper" and "lower" refer to the right position of the device represented in the drawings.

The invention applies more specifically to devices of the single dose of powder type, such as that represented in the Figures. Of course, other types of nasal powder delivery devices can also be considered.

The device 100 represented in the Figures comprises a reservoir 110 containing one single dose of powder. Devices with a reservoir containing more than one dose are possible. Likewise, devices comprising several reservoirs each containing one single dose are also possible.

A nasal delivery head 120 is assembled on said reservoir 110, said head being intended to be inserted in a nostril of a user. Said nasal delivery head comprises a delivery aperture 121. The delivery head 120 advantageously comprises a finger rest 122 extending radially to facilitate the actuation. A hollow sleeve 123 extends axially upwards from said finger rest 122 and ends at said delivery aperture 121. Preferably, this hollow sleeve 123 is of reduced radial dimension to be able to be inserted in a nostril at the time of the actuation. On the opposite side of the finger rest 122, a skirt 125 extends axially downwards from said finger rest 122. Said skirt 125 comprises, in the vicinity of its axially lower end, a lower flange 127, which radially projects inwards.

The device 100 further comprises an air discharge system 130 generating, upon actuation of said device 100, a flow of compressed air to deliver a dose of powder in said nostril through said delivery aperture 121. Said air discharge system comprises an air chamber 131 and a piston 132 sealingly sliding in said air chamber 131 to compress the air contain in said air chamber 131 and thus generate said flow of compressed air. The piston 132 comprises an upper lip 132a and a lower lip 132b. The air chamber 131 is formed by a hollow axial cylinder 128 which is rigidly connected, preferably as one piece, to the finger rest 122 of the delivery head 120. The lower side of said hollow cylinder 128 is open and blocked by said piston 132. The skirt 125 is arranged around said hollow cylinder 128, and can in particular be formed by a hollow sleeve fixed, for example snap-fitted, in the finger rest 122 of the delivery head 120. The lower flange 127 of the skirt 125 forms a lower abutment for the piston 132, in particular for its lower lip 132b, as can be seen in FIG. 1.

The piston 132 is preferably rigidly connected to an actuation member 140 which the user will press upon the actuation to move the piston 132 in the air chamber 131.

In the example represented in the Figures, the reservoir 110 is formed by a hollow tube 111 open at its two axial ends, and closed at its proximal end by a closing element 112, such as a ball, and closed at its distal end by an insert 115. This insert 115 comprises an axial extension forming a rod, and can, upon actuation, slide in said hollow tube 111 to discharge said closing element 112 outside of its closing position. In this example, the piston 132 of the air discharge system 130 is rigidly connected to an axial projection 135 which extends in the proximal direction, and which, during actuation, will move together with the piston 132 during the compression of the air contained in the air chamber 131. When said projection 135 of the piston 132 comes into contact with said insert 115 of the reservoir 110, a continuation of the piston 132 will cause the sliding of said insert 115 in said hollow tube 111 outside of its closing position. Said insert 115 will, on the one hand, open the passage between the air discharge system 130 and the reservoir 110 and, on the other hand, cause the expulsion of the closing element 112. Thus, the air compressed in the air chamber 131 will flow into said reservoir and drive the dose of powder outside of said reservoir in the direction of said delivery aperture 121. Documents WO9946055, WO0245866, WO2015001281 and WO2017118827 describe devices of this type. Of course, other types of devices are also possible.

According to the invention, the hollow axial cylinder 128 which forms the air chamber 131 comprises a radial shoulder 129. This radial shoulder 129 defines in the side wall of said cylinder 128, a profile that the piston 132, in particular its upper lip 132a, must overcome at the start of actuation. This radial shoulder 129 therefore forms a resistance to actuation that the user must overcome at the start of actuation, and therefore transport security to avoid accidental actuation of the device.

Said radial shoulder 129 connects a first cylinder portion 128a of larger diameter and a second cylinder portion 128b of smaller diameter. Before actuation, the piston 132 is arranged at the first cylinder portion 128a, such that it does not necessarily sealingly cooperate with the cylinder 128. Thus, at rest, the air chamber 131 is advantageously open to the atmosphere. Upon actuation, the piston 132 sealingly cooperates with the second cylinder portion 128b, to compress the air contained in the air chamber 131 and thus generate the flow of compressed air.

As can be seen in FIGS. 1 and 2, the piston 132 can, before actuation, move between two non-actuated positions, a so-called lower transport position, which can be seen in FIG. 1, and an upper transport position, which can be seen in FIG. 2. In the lower transport position, the lower lip 132b of the piston 132 is abutted against the lower flange 127 of the skirt 125. In the upper transport position, the upper lip 132a of the piston 132 is abutted against the radial shoulder 129 of the cylinder 128. Thus, at rest, the piston 132 is in any position located between the two transport positions, and in case of accidental fall, the device is therefore not static, as would be the case if the piston was fixed to the skirt by breakable bridges. While such breakable bridges could be broken in case of fall, for example during a drop test, nothing of the sort with the radial shoulder 129 of the present invention. The transport security and the resistance to falls are therefore improved with the present invention.

Said skirt 125, in the lower portion of its side wall, in the vicinity of the lower flange 127, comprises at least one profile which radially projects inwards 126. These profiles 126 can advantageously be formed by one or more axial ridges, for example three or four ridges distributed over the periphery of the skirt 125. These profiles 126 cooperate with the lower lip 132b of the piston 132 before actuation, i.e. when the piston 132 is located between its lower and upper transport positions, which can be seen in FIGS. 1 to 3. This is only at the start of the actuation, which can be seen in FIG. 4, that the lower lip 132b is released from said profiles 126. The presence of these profiles 126 reinforces the cooperation by friction between the piston 132 and the skirt 125, and therefore contributes to transport security.

A combination of the radial shoulder 129 of the hollow axial cylinder 128 and the profiles 126 of the skirt 125 provides an optimal result relating to transport security, while allowing to predetermine, with greater precision, the force threshold necessary for the user to actuate the device, compared with breakable bridges, for example. In addition, both the radial shoulder 129 and the profiles 126 are less difficult to mould than breakable bridges, and the present invention therefore allows to simplify the manufacturing and the assembly of the device.

The present invention has been described in reference to one advantageous embodiment, but it is understood that a person skilled in the art can apply any modifications to it, without moving away from the scope of the present invention such as defined by the appended claims.

The invention claimed is:

1. A nasal powder delivery device comprising a reservoir containing at least one dose of powder, a nasal delivery head intended to be inserted in a nostril of a user, said nasal delivery head comprising a delivery aperture, and an air discharge system generating, upon actuation of said nasal powder delivery device, a flow of compressed air to deliver a dose of powder in said nostril through said delivery aperture, said air discharge system comprising an air chamber, formed by a hollow axial cylinder and a piston which, upon actuation of the device, sealingly slides in said air chamber to compress the air contained in said air chamber, said hollow axial cylinder comprises a radial shoulder which connects a first cylinder portion of larger diameter and a second cylinder portion of smaller diameter, said piston being arranged before actuation at said first cylinder portion, and upon actuation, said piston sealingly cooperates with said second cylinder portion, to compress the air contained in said air chamber, and thus generate the flow of compressed air, said radial shoulder defining in said hollow axial cylinder, a profile that said piston must overcome at the start of actuation, said piston comprising an upper lip and a lower lip, a skirt being arranged around said hollow axial cylinder, said skirt comprising, in the vicinity of its axially lower edge, a lower flange, which radially projects inwards, characterised in that said skirt comprises, in the vicinity of said lower flange, at least one profile, which radially projects inwards cooperating before actuation with said lower lip of said piston.

2. The device according to claim 1, wherein, before actuation, said piston can be moved between two non-actuated positions, a lower transport position, in which said lower lip of said piston is abutted against said lower flange of said skirt, and an upper transport portion, in which said upper lip of said piston is abutted against said radial shoulder of said hollow cylinder.

3. The device according to claim 1, wherein said profiles are formed by one or more axial ridges distributed over the periphery of said skirt.

4. The device according to claim 1, wherein said air chamber is open to the atmosphere before actuation.

5. The device according to claim 1, wherein said reservoir contains one single dose of powder, distributed upon one single actuation of said nasal powder delivery device.

\* \* \* \* \*